(12) United States Patent
Monstadt et al.

(10) Patent No.: US 11,229,439 B2
(45) Date of Patent: Jan. 25, 2022

(54) BAND-SHAPED OCCLUSION MEANS

(71) Applicant: femtos GmbH, Bochum (DE)

(72) Inventors: Hermann Monstadt, Bochum (DE); Hans Henkes, Stuttgart (DE); Ralf Hannes, Dortmund (DE)

(73) Assignee: Femtos GmbH, Bochum (DE)

( * ) Notice: Subject to any disclaimer, the term of this patent is extended or adjusted under 35 U.S.C. 154(b) by 504 days.

(21) Appl. No.: 15/778,995

(22) PCT Filed: Nov. 24, 2016

(86) PCT No.: PCT/EP2016/078658
§ 371 (c)(1),
(2) Date: May 24, 2018

(87) PCT Pub. No.: WO2017/089451
PCT Pub. Date: Jun. 1, 2017

(65) Prior Publication Data
US 2018/0353187 A1 Dec. 13, 2018

(30) Foreign Application Priority Data
Nov. 26, 2015 (DE) .................... 10 2015 120 554.8

(51) Int. Cl.
*A61B 17/12* (2006.01)
*A61B 17/00* (2006.01)

(52) U.S. Cl.
CPC .... *A61B 17/12145* (2013.01); *A61B 17/1215* (2013.01); *A61B 17/12031* (2013.01); *A61B 17/12113* (2013.01); *A61B 17/12163* (2013.01); *A61B 17/12172* (2013.01); *A61B 17/12177* (2013.01); *A61B 2017/00867* (2013.01); *A61B 2017/00893* (2013.01);
(Continued)

(58) Field of Classification Search
CPC ........ A61B 17/12145; A61B 17/12172; A61B 17/12031; A61B 17/12113; A61B 17/1215; A61B 17/12163; A61B 17/12168; A61B 17/12022; A61B 17/12036
See application file for complete search history.

(56) References Cited

U.S. PATENT DOCUMENTS

| | | | | |
|---|---|---|---|---|
| 6,428,558 | B1 * | 8/2002 | Jones et al. | A61B 17/00 606/200 |
| 6,855,154 | B2 * | 2/2005 | Abdel-Gawwad | A61M 29/00 606/200 |

(Continued)

FOREIGN PATENT DOCUMENTS

WO WO2012034135 3/2012

*Primary Examiner* — Sarah A Simpson
(74) *Attorney, Agent, or Firm* — Crockett & Crockett, PC; K. David Crockett, Esq.

(57) ABSTRACT

The invention relates to an implant for vascular applications that can be transported by means of a catheter and is intended in particular to influence the blood flow in the area of arteriovenous malformations, such as fistulas and aneurysms, to fill the saclike dilation of the malformation, promote thrombus formation and cover the neck of the malformation. The implant according to the invention is provided with an occlusion unit (1, 13) having a three-dimensional shape constructed from several subunits (5a, 14) from a framework of struts (5, 16, 17), with a covering, preferably a membrane (6), being located between struts (5, 16, 17).

24 Claims, 3 Drawing Sheets

(52) U.S. Cl.
CPC .......... *A61B 2017/12054* (2013.01); *A61B 2017/12063* (2013.01); *A61B 2017/12068* (2013.01)

(56) References Cited

U.S. PATENT DOCUMENTS

| | | | | |
|---|---|---|---|---|
| 2006/0020286 | A1* | 1/2006 | Niermann | A61F 2/01 |
| | | | | 606/200 |
| 2009/0112251 | A1* | 4/2009 | Qian | A61B 17/12163 |
| | | | | 606/194 |
| 2015/0250628 | A1* | 9/2015 | Monstadt | A61F 2/90 |
| | | | | 623/1.16 |
| 2015/0305750 | A1* | 10/2015 | Hadley | A61B 17/12109 |
| | | | | 606/194 |
| 2015/0343181 | A1* | 12/2015 | Bradway | A61B 17/12031 |
| | | | | 604/103.1 |

* cited by examiner

Fig. 2
Fig. 3
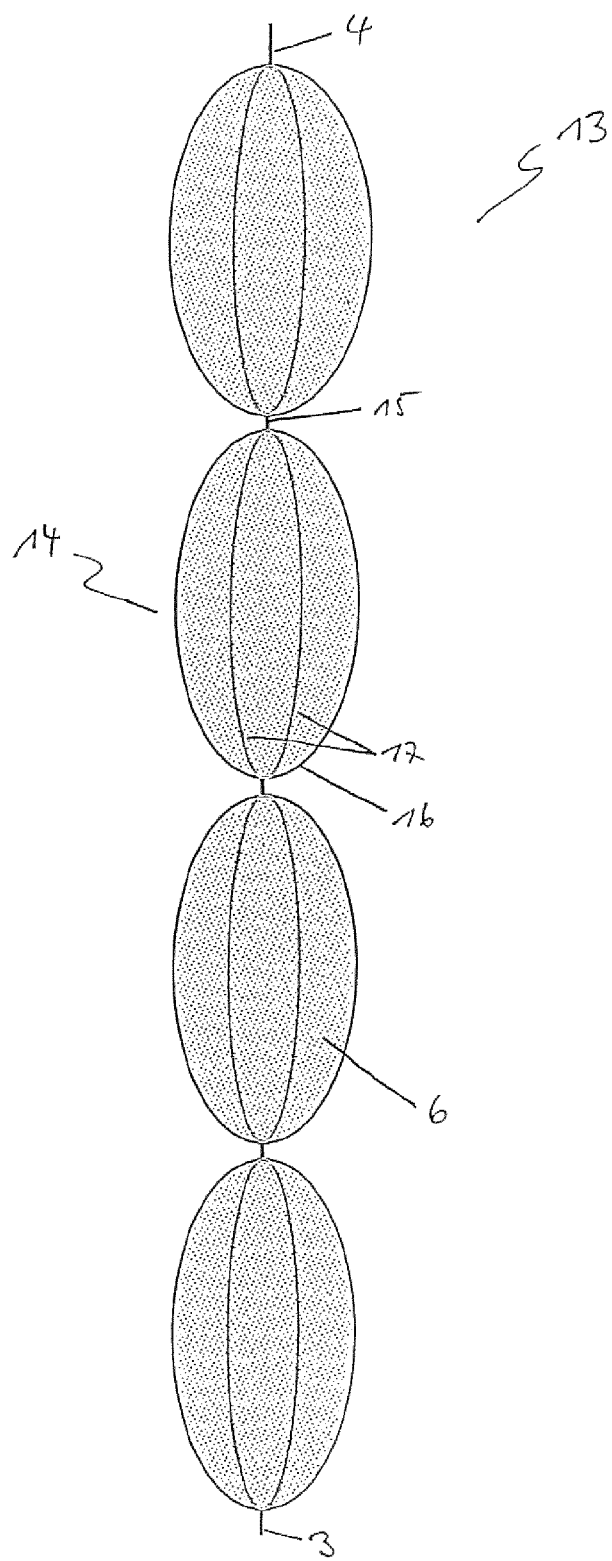
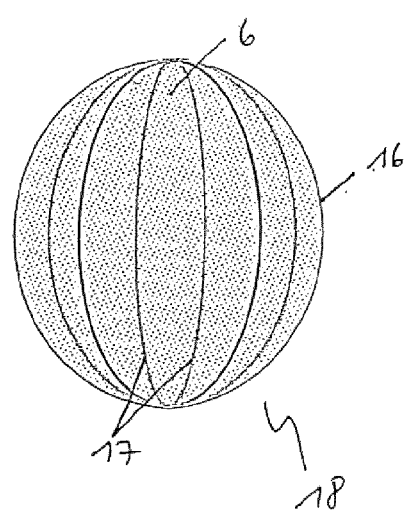

BAND-SHAPED OCCLUSION MEANS

FIELD OF THE INVENTIONS

The invention relates to an implant for vascular applications that can be transported by means of a catheter and is intended in particular to influence the blood flow in the area of arteriovenous malformations, such as fistulas and aneurysms, to fill the saclike dilation of the malformation and to promote thrombus formation.

BACKGROUND OF THE INVENTIONS

Aneurysms are usually saclike dilatations of the vessel wall and occur primarily in structurally weakened areas of the vessel wall due to the constant pressure of the blood. Therefore, the inner walls of an aneurysm are quite sensitive and susceptible to injuries that can lead to a rupture of the aneurysm sac. As a consequence, considerable health impairments, such as neurological malfunction, may occur that may even lead to the death of the patient. This may primarily be the case if such malformations are occurring in the cerebral area.

Current intravascular methods for the treatment of aneurysms are sufficiently known and in particular pursue two approaches. Either the aneurysm is filled with an occlusion means, with a variety of filling materials and techniques being known from the state of the art here, or access to the aneurysm, such as the neck of an aciniform aneurysm, is closed off from the blood vessel side making use of stent-like implants for this purpose. Both methods serve to reduce the blood flow into the aneurysm and in this way alleviate the pressure acting on the aneurysm, ideally eliminating it.

The filling material, usually platinum coils, is intended to fill the sac of the aneurysm and subsequently undergoes thrombogenesis forming into a more or less compact structure within the aneurysm. There are two problems of this treatment method that may lead to disadvantages encountered in the progression of the disease. On the one hand, the aneurysm is insufficiently filled, which allows the blood supply to the aneurysm to continue and thus results in the pressure to further act on its inner wall. The danger of a continuous expansion of the aneurysm and finally its rupture remains, albeit in an attenuated form. On the other hand, this treatment method is only suitable for aneurysms with a relatively narrow neck—so-called aciniform aneurysms—as otherwise there is the risk that the coils protrude from a wide aneurysm neck into the blood vessel and thrombogenize there, which can lead to occlusions. In the worst case, a coil is completely washed out of the aneurysm and causes vessels to be occluded elsewhere.

To keep the coils in place in the aneurysm sac, the neck of the aneurysm is often additionally covered with a special stent.

Another intravascular treatment approach focusses on so-called flow diverters. These implants are similar in appearance to stents that are used in the treatment of stenosis. However, since the purpose of the flow diverters is not to keep a vessel open, but to obstruct access to the aneurysm on the side of the blood vessel, the mesh width is very narrow; alternatively, implants of this kind are coated with a membrane. The disadvantage of these implants is that there is a risk that existing side branches in the immediate vicinity of the aneurysm to be treated may sometimes be covered as well and thus closed off in the medium or long term.

In WO 2012/034135 A1 an implant has been disclosed that—in various embodiments—takes on a three-dimensional, almost spherical shape when it is liberated within the aneurysm and in this way fills the aneurysm. The basic material for the three-dimensional implant is in any case a mesh-like fabric, the embodiment examples and figures are all based on a tubular braiding comprising shape memory material.

This means for the expanded, three-dimensional state of the implant that sometimes four or more fabric layers are arranged on top of each other so that an unfavorable stiffness is conferred to the almost round implant. Due to the fact that aneurysms are rarely absolutely round, a three-dimensional implant should be able to adapt to the morphology of the aneurysm in the best possible way. What is more, the implant is too voluminous for small-caliber catheters.

It is, therefore, the object of the present invention to provide an occlusion means for the intrasaccular treatment of a vascular aneurysm which, after expansion, takes on a defined, yet at the same time as flexible three-dimensional shape as possible. In addition, the implant is intended to promote the formation of thrombus within the aneurysm and to keep other treatment options open.

SUMMARY

As proposed by the invention, this objective is achieved by the provision of an implant of the kind first mentioned above, in which the occlusion unit takes on a three-dimensional shape after expansion and subsequently is separated from the insertion unit by known techniques of mechanical, electrolytic or thermal detachment from or dissolution of the connection point. The occlusion unit comprises a framework formed from a plurality of struts with a covering spanned between them. The framework can be formed from a variety of wires or obtained by laser cutting. In any case, the material should have shape memory properties, in particular nitinol is conceivable here. The covering is preferably a polymer membrane, especially a nanomembrane obtained by electrospinning, but any other suitable membrane or covering, for example made of a plurality of braided or non-braided wires, is also conceivable. The wires in turn may also be covered with a membrane.

In a first embodiment, the occlusion unit in the stretched arrangement is provided with a central spine and has one or a plurality of arch struts attached to it. Spine and/or arch strut(s) comprise a shape memory material, for example of nitinol. They can also be made of other materials, such as polymers.

The central spine may have a spherical or helical shape imprinted on it, but any other shape is also conceivable. Preference is given to any shapes and forms that lead to the desired three-dimensional design of the implant and prove to be advantageous for intrasaccular expansion. This includes in particular forms and shapes in which the proximal and distal end of the occlusion unit reach into the lumen of the expanded occlusion unit having been placed into the aneurysm sac with a view to preventing injury to the wall of the aneurysm.

When in its stretched or elongated state, the shape of the implant can be supported by an additional supporting wire which can be retracted after implantation. Such an arrangement can simplify the navigation of the stretched implant by means of a catheter. During transport, the support wire runs parallel to the implant and has no three-dimensional shape imprinted on it.

In a variant of the first embodiment, the spine in its stretched/elongated state can also be a coil capable of being stretched to at least the length of an arch strut. In this case, the support wire can pass centrally through the core of the coil and fix and keep the coil at the desired elongation. After expansion, the support wire is retractable and enables the spine to assume its three-dimensional memory shape and does not remain in the implant. The shape characteristics of the coil are in accordance with those of the solid variant described hereinbefore.

In another variant of the first embodiment the spine can be provided in the form of a tube. In this case, the supporting wire can pass centrally through the tube and in this way keep the tube in its stretched state. After expansion, the supporting wire is retractable and thus enables the tubular spine to assume its three-dimensional memory shape and does not remain in the implant. The shape characteristics of the tube are in accordance with those of the solid variant described above.

The arch strut or arch struts can have a sinusoidal configuration when in (partially) expanded condition. If one imagines an arch strut in a coordinate system, the axial spine forms the x-axis and the arch strut forms the sine curve. At the intersections of axial spine and arch strut, this arch strut can be secured to the spine. The shape formed by the axial spine and a curve of the superimposed arch strut is hereinafter referred to as wing. If one refers—for illustrative purposes only—to a sine wave, the curve of the arch strut corresponds to half a sine wave and the corresponding section of the spine to half a period length. For simplification and with respect to the area of the wing, only the spine section and the curve of the arch struts are to be referred to hereinafter. Likewise, the size of a wing shall be defined below by the ratio of its width (of the axial spine section) to its length (the maximum amplitude of the corresponding section of the arch strut curve).

In the event the occlusion unit comprises a spine and only one arch strut, 2 to 30, preferably 4 to 10 of these wings are formed. However, the number of wings also depends on the size of the implant. It may prove to be expedient to manufacture implants having larger diameters suited for large aneurysms, even with more than 30 wings.

In another variant of the first embodiment, two arch struts can also be attached to a spine in such a way that the wings are alternately arranged. In this case, the second arch strut is arranged in particular axisymmetrically with respect to the axial spine. The wings formed by both arch struts are preferred, but not necessarily to lie in one plane. In the event the occlusion unit comprises a spine and two arch struts, 4 to 40, preferably 8 to 20 of these wings are formed. Embodiments comprising 40 or more wings are conceivable for implants having a large diameter to suit large aneurysms.

Conceivable as well are embodiments comprising a plurality of arch struts being provided with a plurality of wings. It is also conceivable that the wings do not lie in a single plane but are arranged for example spirally or in another way around the spine in order to achieve the desired three-dimensional shape in the expanded state.

The wings can be of the same or different sizes. If they are arranged so as to be sinusoidal, the amplitude and/or period length may decrease from proximal to distal—or vice versa. An alternating size variation or an arrangement that follows another pattern is also conceivable.

Aside from the sinusoidal form all other shapes are also conceivable.

The size of a wing as defined by the ratio of the axial spine section to the maximum amplitude of the pertinent section of the arch strut curve varies depending on the relevant embodiment.

The length of a wing will as a rule not deviate significantly from $\frac{1}{4}(2\pi r)$, where $r=d/2$ and d is the diameter of the implant. Individual wings of the same implant may also deviate more strongly from this length if this is advantageous with respect to creating the desired three-dimensional shape.

The width of the corresponding spine section depends on the number of wings to be provided in the implant. If all wings are assumed to be of the same width, this means a width of $(2\pi r)/2n$ for n wings in an alternating arrangement and $(2\pi r)/n$ for n wings in an opposite arrangement. In the event individual wings overlap, the width may reduce further. Individual sections of the same implant may also deviate more strongly from this width if this is advantageous with respect to creating the desired three-dimensional shape.

The area of the wings is provided with a covering. This covering comprises a polymer membrane, preferably a polyurethane film or a nanomembrane of polycarbonate urethane (PCU), which is produced by electrospinning. Said membrane can be fixed to the arch strut and axial wire or just to the arch strut. In case the axial wire is designed as a coil, it is advisable to attach the membrane exclusively to the arch strut. However, a covering comprising a polymer mesh, polymer threads, wires or a wire grid or wire braiding is also conceivable and possible.

With a view to increasing the thrombogenicity of the implant, thrombogenic materials, such as nylon filaments, can be spun or braided into the membrane. The membrane, the covering or, as the case may be, the arch struts or the axial wire can be coated with thrombogenic substances.

Aimed at stabilizing the membrane, the nylon filaments can be attached with one end each to the arch strut and/or axial spine. In a preferred embodiment, the filaments extend perpendicularly to the spine. Nevertheless, any other run is also conceivable. In another preferred embodiment, the filaments extend in parallel to the axial spine and are fixed at their ends only to the arch strut. Moreover, embodiments may be used that combine both options.

In case the spine is designed in the form of a coil, it is recommendable to attach the filaments exclusively to the arch strut.

In its expanded form the occlusion unit is of three-dimensional shape. In this context, ball-shaped, spherical or even ovoid figures are possible. Amorphous forms are also conceivable, as are helical structures. In expanded three-dimensional shape, the wings of the occlusion unit may overlap but need not necessarily overlap.

To bring the occlusion unit into a stretched/elongated configuration as needed for navigation by means of the catheter, the wings must be placed against the spine. Various options can be used for this purpose. As described hereinbefore, the spine can be provided in the form of a coil or spiral capable of being stretched to the length of the arch struts. It would also be conceivable that the arch struts are movably attached to the spine or that the wings are rolled up around the spine.

In a second embodiment, the occlusion unit comprises several struts with a covering spanned between them. In particular, this covering may comprise a polymer membrane, preferably a nanomembrane, which is produced by electrospinning. However, a covering comprising a polymer film, a polymer braiding, polymer threads, wires or a wire grid or wire braiding is also conceivable and possible. In case the covering is a polymer membrane, a polyurethane in the form of a film or an electrospun fabric is particularly suitable. Preferably, such a polyurethane film is particularly thin, for example has a thickness of about 25 nm.

In the stretched/elongated form required for transportation within the catheter, the struts are arranged almost parallelly. The two outermost struts, that could also be referred to as frame struts, form the outer frame of the occlusion unit. The intermediately situated struts, which could also be referred to as intermediate struts, are conducive to forming the three-dimensional structure of the expanded occlusion unit.

With a view to increasing the thrombogenicity of the implant, thrombogenic materials, such as nylon filaments, can be spun into the covering. The covering or, if thought expedient, the struts can also be coated with thrombogenic substances.

After expansion has been completed, the struts form lined-up subunits whose three-dimensional structure is shell-like. Between the subunits and at the distal and proximal end of the occlusion unit, the struts are arranged so as to be directly adjacent to each other. At these points, hereinafter referred to as interspaces, the struts may lie adjacent to each other in unconnected form, may be twisted, may intersect, be welded or otherwise secured.

All struts forming the subunits pass through the entire occlusion unit from proximal to distal. In the event of laser-cut frames, these are as a rule cut from a single part, which may also be a tube. However, also conceivable are embodiments in which the individual subunits are manufactured separately and are only connected linearly to one another by means of additional wires.

After expansion has taken place, the shell-like subunits in their entirety form a spherical shape, which in particular is ball-shaped or ovoid in shape. Other forms are conceivable as well.

In a preferred variant of the second embodiment of the implant proposed by the invention, the framework of the occlusion unit comprises 4 struts. Moreover, the relevant occlusion unit preferably comprises 6 subunits. It may be considered expedient to produce implants of large size with significantly more than 4 struts and 6 subunits. Conceivable are embodiments comprising up to 12 struts and 20 subunits for implants meant to treat large aneurysms.

The shape of the subunits can be identical, i.e. all subunits of the occlusion unit have the same shape and size. However, embodiments are conceivable in which this is not the case.

It is particularly conceivable that the subunit located at the proximal and distal ends may have a different shape, which, for example, may prove to be beneficial for expansion, catheter navigation and guidance or the fabrication of the implant proposed by the invention.

It is moreover conceivable to have embodiments in which several subunits may differ, for example through a continuous or alternating or otherwise determined increase or decrease in size from one end of the implant to the other.

In an alternative embodiment, the occlusion unit of the inventive implant comprises a single strut or an occlusion coil.

Should the occlusion unit comprise a single strut, this is preferably a single wire made of a material having shape-memory characteristics, with all that has been described so far with respect to the materials of the embodiments mentioned hereinbefore applying to this alternative embodiment as well. The wire is coated with a membrane, in particular with a nanomembrane produced by an electrospinning process. In a first configuration that involves transportation by means of the catheter, the wire is stretched linearly. In a second configuration which is impressed on the shape memory material, the wire takes on its three-dimensional spatial structure after having been released from the catheter. This three-dimensional shape can be spherical or ovoid according to the embodiments described hereinbefore, however, it is also possible to have convoluted, helical or other forms that are suitable for filling a sac-like structure in single, plural or multiple number.

If the occlusion unit is a coil, said coil being also covered with a membrane, in particular a nanomembrane produced by an electrospinning process. The membrane covers the outside of the coil in a preferred embodiment in a socklike fashion from its distal to its proximal end, with the membrane adhering to the coil surface. Alternatively, a conceivable fixation method is to secure the membrane at the distal and proximal end of the occlusion unit. In this manner, the membrane is kept slightly movable on the coil surface and allows the flexibility of the implant to be maintained. At the same time, it acts as a stretch resistance element that prevents the coil from losing its primary shape. In additional embodiments, the membrane can also be provided to cover the coil only partially. It is also conceivable that the membrane is not only applied to the outer surface of the coil, but also to its inner surface or parts thereof.

The coil comprises a wire made of platinum or a platinum alloy, in particular a platinum-iridium alloy. In the interior of the coil there may be a wire of shape memory material that gives the coil a secondary three-dimensional shape after said coil has been released from the catheter. At the same time, the inner wire serves as a stretch resistance element, whereby the stretching resistance is further improved by the application of a membrane as proposed by the invention. The three-dimensional shape of the coil can be spherical or ovoid according to the embodiments described hereinbefore, however, it is also possible to have convoluted, helical—in the form of a coiled coil for example—or other forms that are suitable for filling a sac-like structure in single, plural or multiple number.

With a view to increasing the thrombogenicity of the implant, thrombogenic materials can be spun into the membrane such as nylon filaments, for example. The covering or, if thought expedient, the struts and wires can also be coated with thrombogenic substances.

In all other respects, all statements made in connection with the embodiments mentioned hereinbefore, in particular also regarding the material of the membrane or other additional substances, apply to this embodiment as well.

The disadvantages of coils as filler elements for aneurysms as they have been described at the beginning are greatly reduced by coating with a membrane of the type detailed hereinbefore. The coating or covering of the wires or coils of the occlusion unit according to the invention means that the expanded occlusion unit is anchored much better in the aneurysm sac, and, furthermore, the formation of a thrombus is also significantly accelerated.

Both effects are based on the greatly increased surface area of an implant covered with a nanomembrane in comparison to an uncoated implant.

BRIEF DESCRIPTION OF THE DRAWINGS

The invention is now described in detail as follows with reference being made to the figures showing the respective embodiments, where FIG. 2 is a schematic drawing of a first variant of the second embodiment 13 of the occlusion unit comprising four uniformly designed subunits 14 in partially expanded view external to a catheter, FIG. 3 is a schematic drawing of the second embodiment 13 of the occlusion unit according to the invention in fully expanded view 18 external to the catheter.

DETAILED DESCRIPTION OF THE INVENTIONS

Figure 1:
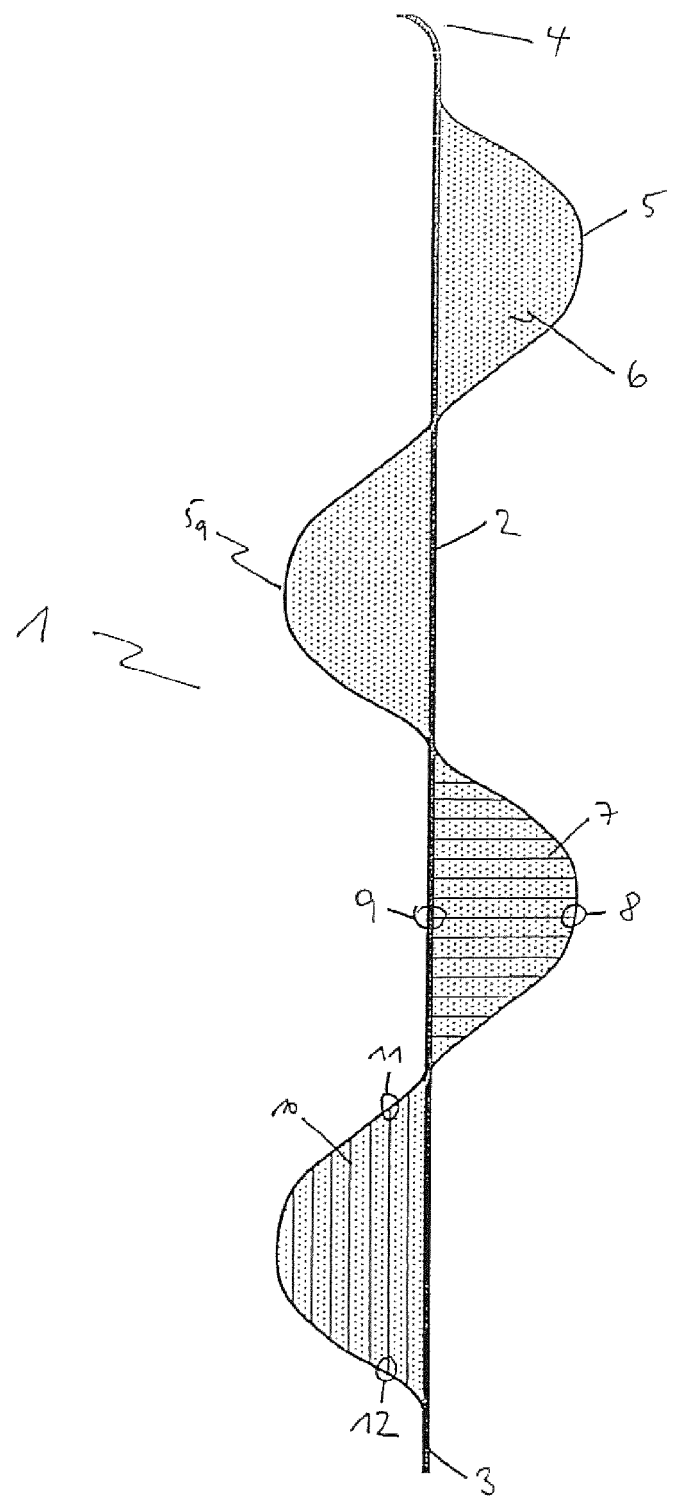
FIG. 1 shows a first embodiment of occlusion unit 1 of the implant according to the invention in partially expanded view external to a catheter comprising an axial spine 2, an arch strut 5 with covering 6, and nylon filaments 7, 10.

FIG. 1 illustrates the first embodiment 1 of the occlusion unit of the implant proposed by the invention in partially expanded, stretched, two-dimensional view situated outside of the catheter, without the final three-dimensional shape being assumed. The centrally extending axial spine 2 with proximal 3 and distal 4 ends, an arch strut 5 forming the wings 5a with membrane 6 and nylon filaments 7, 10 which—in the case of arrangement 7 perpendicular to the spine 2—are fastened to the arch strut 5, 8 and to the spine 2, 9, or in the case of arrangement 10 run parallel to the axial strut 2 with both ends 11, 12 being secured to the arch strut 5.

FIG. 2 is a schematic drawing of a first variant of the second embodiment 13 of the implant according to the invention in partially expanded, stretched, two-dimensional view situated outside of the placement catheter, without the final three-dimensional shape being assumed (see FIG. 3, numeral 18). The four uniformly designed subunits 14 are formed by struts 16, 17, which are provided with a covering 6. The frame of the occlusion unit is formed by two frame struts 16. Two intermediate struts 17 arranged between the frame struts 16 are used for further three-dimensional shaping, said intermediate struts lie side by side in the spaces 15 between the subunits 14 and at the respective proximal 3 and distal 4 ends or are connected to each other.

FIG. 3 is a schematic drawing of the second embodiment 13 of the implant proposed by the invention in expanded view 18 situated external to the catheter. The implant has taken on its final three-dimensional shape. The sphere is formed by the frame 16 and intermediate struts 17 and by the covering 6, which is spanned between them. The subunits form individual spherical shell segments that join to form into a ball.

Figure 4:
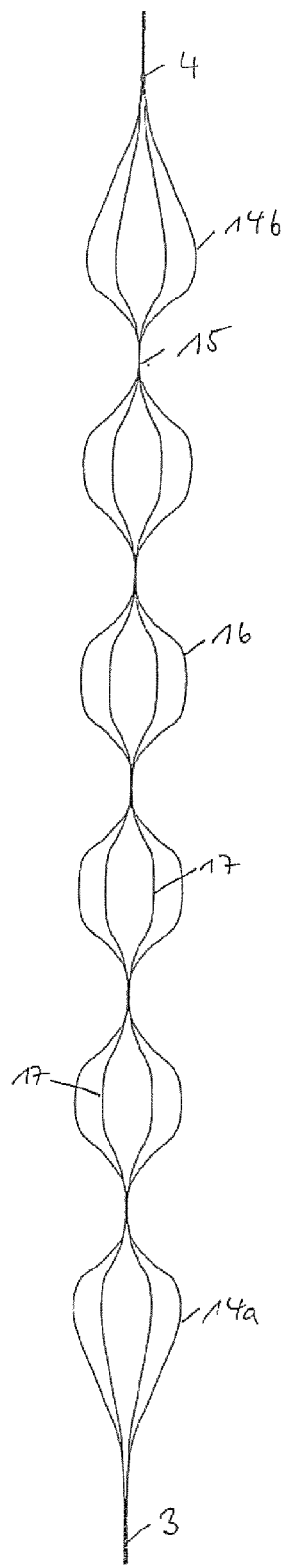
FIG. 4 is a schematic drawing of a second variant of the second embodiment 13 in partially expanded view external to a catheter, with six subunits 14, FIG. 5 corresponds to FIG. 4, with the framework solely being formed by the frame struts 16.

FIG. 4 illustrates schematically a second variant of the second embodiment 13 of the implant according to the invention in partially expanded, stretched, two-dimensional view situated outside of the catheter, without the final three-dimensional shape (see FIG. 3, numeral 18) being assumed. The six subunits 14 of this embodiment are not identical with each other. The first proximal and first distal subunits differ from the four subunits arranged in between in that the first proximal subunit has a pointed configuration towards its proximal end and the first distal subunit has a pointed configuration towards its distal end. The four subunits arranged in between are identical in shape. The subunits are formed by struts 16, 17, which have a covering which is not shown in this illustration. The frame of the occlusion unit is formed by two frame struts 16. Two intermediate struts 17 arranged between the frame struts 16 are used for further three-dimensional shaping, said intermediate struts lie side by side in the spaces 15 between the subunits 14 and at the respective proximal 3 and distal 4 ends or are connected to each other.

Figure 5:
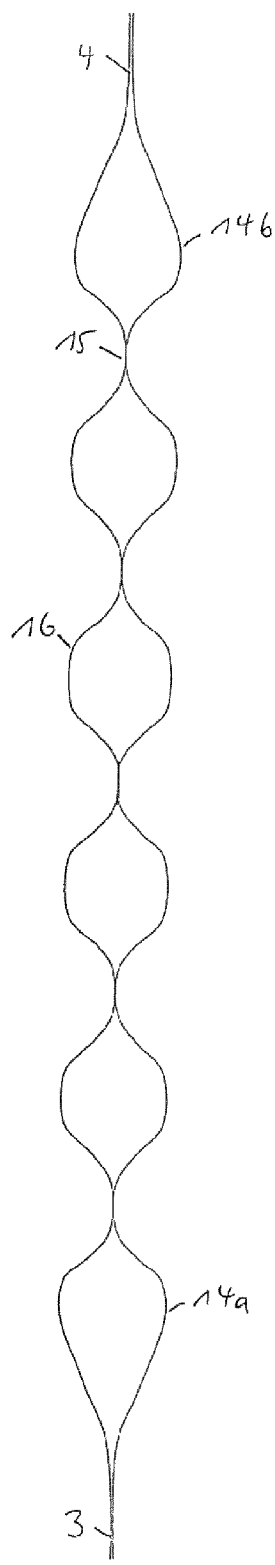

FIG. 5 corresponds to FIG. 4, with the framework solely being formed by the frame struts 16.

The invention claimed is:

1. An implant system for treating an arteriovenous malformation comprising an occlusion unit, with the occlusion unit comprising several subunits, with the subunits comprising a framework having shape memory properties and being formed from wire or produced by laser cutting, wherein the framework is constructed of one or more struts and the occlusion unit being provided with a first stretched arrangement suited for transportation by means of a catheter and a second expanded arrangement after exit from the catheter, wherein the occlusion unit takes on a three-dimensional shape in the second expanded arrangement of said occlusion unit, characterized in that:

a covering is located between the one or more struts of the framework of the occlusion unit; and the framework of the occlusion unit comprises a central axial spine and the one or more struts attached thereto, wherein the axial spine can be supported during placement navigation by means of the catheter and for subsequent release of the framework in the arteriovenous malformation in a stretched state by an additional supporting wire which can be removed after release of the occlusion unit; wherein the one or more struts intersect with the axial spine at a first end and a second end of each strut, with the first end of each strut intersecting the axial spine and secured to the axial spine at a respective first point of intersection, and with the second end of each strut intersecting the axial spine and secured to the axial spine at a respective second point of intersection.

2. An implant system according to claim 1, characterized in that the covering comprises a membrane made of polymer material.

3. An implant system according to claim 2, characterized in that the membrane comprises a nanomembrane produced by an electrospinning process.

4. An implant system according to claim 2, wherein the membrane comprises polyurethane.

5. An implant system according to claim 1, characterized in that the covering comprises wires, wherein the wires are braided.

6. An implant system according to claim 1, characterized in that in an expanded state the one or more struts form wings arranged opposite or alternately in sinusoidal or other form, with the axial spine corresponding to an x-axis and the one or more struts corresponding to a function curve, and a strut surface of a wing corresponding to the surface which lies between two intersection points of the function curve with the x-axis and said strut surface of the wing is enclosed by the corresponding sections of the function curve and the x-axis.

7. An implant system according to claim 6, characterized in that at least 3 of the wings are located on the axial spine when arranged alternately and at least 6 of the wings are located on the axial spine when arranged oppositely.

8. An implant system according to claim 7, characterized in that each of the wings has an identical shape and/or size in the expanded state.

9. An implant system according to claim 7, characterized in that at least a first one of any of the wings in the expanded state has a different shape and/or size than a second one of any of the wings, with a sinusoidal shape the amplitude and/or the period length which decreases from proximal to distal or from distal to proximal.

10. An implant system according to claim 7, characterized in that each of the wings has a different shape and/or size in the expanded state.

11. An implant system according to claim 1, characterized in that a surface generated by at least one of the one or more struts in an expanded state is additionally reinforced by one or a plurality of filaments which are attached solely to the at least one of the one or more struts and run parallel to the axial spine.

12. An implant system according to claim 11, characterized in that the axial spine is an expandable coil or spiral, wherein in the stretched state of the axial spine, the axial spine has a length that approximately corresponds to a length of at least one of the one or more struts in a stretched state of said at least one of the one or more struts.

13. An implant system according to claim 11, characterized in that the occlusion unit forms a spherical or ovoid shape in the expanded state.

14. An implant system according to claim 1, characterized in that a surface generated by at least one of the one or more struts in an expanded state is reinforced by one or a plurality of filaments, wherein one end of the respective filament is connected to the at least one of the one or more struts and the other end is connected to the axial spine, so that the respective filament is aligned perpendicularly to the axial spine.

15. An implant system according to claim 1 characterized in that a surface generated by at least one of the one or more struts in an expanded state is additionally reinforced by a first one or a first plurality of filaments which are attached solely to the at least one of the one or more struts and run parallel to the axial spine, and characterized in that the surface generated by the at least one of the one or more struts in the expanded state is reinforced by a second one or a second plurality of filaments, wherein one end of a respective second one or the second plurality of filaments is connected to the at least one of the one or more struts and the other end to the axial spine, so that the respective second one or the second plurality of filaments is aligned perpendicularly to the axial spine.

16. An implant system according to claim 1, characterized in that the framework of the occlusion unit comprises at least 2 of the one or more struts.

17. An implant system according to claim 1, wherein:
a first one of the several subunits comprises a first plurality of the one or more struts characterized in that said first plurality of the one or more struts of the first one of the several subunits extend in a first stretched state substantially parallel to one another and, in an expanded state, form a first three-dimensional subunit; and
a second one of the several subunits comprises a second plurality of the one or more struts characterized in that said second plurality of the one or more struts of the second one of the several subunits extend in a second stretched state substantially parallel to one another and, in an expanded state, form a second three-dimensional subunit, and
said second three-dimensional subunit is disposed on the axial spine proximal to the first three-dimensional subunit.

18. An implant system according to claim 17, characterized in that the struts of one of the first or second plurality of the one or more struts are connected to one another at points of contact and are twisted and/or welded to one another.

19. An implant system according to claim 17, characterized in that the first one of the several subunits and the second one of the several subunits have an identical shape and/or size.

20. An implant system according to claim 19, characterized in that the each of the several subunits form a spherical or ovoid shape in the second expanded arrangement.

21. An implant system according to claim 17, characterized in that the first one of the several subunits differs in shape or size from the second one of the several subunits.

22. An implant system according to claim 17, characterized in that each of the several subunits differ in shape and/or size from all remaining subunits of the several subunits.

23. An implant according to claim 1, characterized in that the covering contains a thrombogenic additive.

24. An implant system according to claim 23, characterized in that the thrombogenic additive comprises nylon filaments.

* * * * *